United States Patent [19]

Nambu et al.

[11] Patent Number: 4,808,353

[45] Date of Patent: Feb. 28, 1989

[54] PROCESS FOR PREPARING AN ARTIFICIAL BIOLOGICAL MEMBRANE

[75] Inventors: Masao Nambu, Yokohama; Tatsuo Kinoshita, Kanagawa; Mineo Watase, Shizuoka, all of Japan

[73] Assignee: Nippon Oil Co., Ltd., Tokyo, Japan

[21] Appl. No.: 816,966

[22] Filed: Jan. 8, 1986

Related U.S. Application Data

[63] Continuation of Ser. No. 534,235, Sep. 21, 1983, abandoned.

[30] Foreign Application Priority Data

Sep. 24, 1982 [JP] Japan .................. 57-164870

[51] Int. Cl.$^4$ .............. C08J 5/00; C08J 3/00; C08J 3/18

[52] U.S. Cl. ................... 264/28; 424/78; 424/81; 424/423; 424/424; 623/66; 623/901; 252/315.1; 264/234; 264/237; 264/345; 264/348; 264/DIG. 60

[58] Field of Search .......... 264/28, 234, 237, 345, 264/348, DIG. 60; 426/524, 573, 1; 252/315.1; 424/423, 78, 81, 424; 427/2; 525/54.1; 604/5, 4, 6, 891; 623/66, 901

[56] References Cited

U.S. PATENT DOCUMENTS

| | | | |
|---|---|---|---|
| 3,236,653 | 2/1966 | Vranelen et al. | 525/54.1 |
| 3,826,678 | 7/1974 | Hoffman et al. | 604/5 |
| 3,875,302 | 4/1975 | Inoue | 426/1 |
| 4,087,808 | 8/1987 | Javett et al. | 604/4 |
| 4,415,490 | 11/1983 | Joh | 525/54.2 |
| 4,452,776 | 6/1984 | Refojo | 604/891 |

FOREIGN PATENT DOCUMENTS

| | | | |
|---|---|---|---|
| 0012854 | 4/1972 | Japan . | |
| 48-30462 | 9/1973 | Japan . | |
| 49-42479 | 11/1974 | Japan . | |
| 54-01501 | 1/1979 | Japan . | |
| 322165 | 4/1972 | U.S.S.R. | 427/2 |
| 502277 | 2/1976 | U.S.S.R. | 427/2 |

OTHER PUBLICATIONS

Foakes, E. H., "Simple Method to Determine the Pre-Gelation Temp. of a PVC Plastisol", British Plastics, 2/66.

*Primary Examiner*—Jan H. Silbaugh
*Assistant Examiner*—Hubert C. Lorin
*Attorney, Agent, or Firm*—Jordan and Hamburg

[57] ABSTRACT

A process for preparing an artificial biological membrane in which an aqueous solution containing 6 wt % or more of polyvinyl alcohol having a degree of hydrolysis of not less than 95 mol % and an average polymerization degree of not less than 700 and containing a biological substance or a substance which does not hinder the gelation of the polyvinyl alcohol is subjected to a freezing step followed by a thawing step. Then, the mass thus obtained is further subjected to at least one additional cyclic processing step including the freezing and thawing steps. The product hydrogel is hard or not too soft and not swollen in water.

5 Claims, No Drawings

PROCESS FOR PREPARING AN ARTIFICIAL BIOLOGICAL MEMBRANE

This application is a continuation of application Ser. No. 534,235, filed 9/21/83, now abandoned.

BACKGROUND OF THE INVENTION

1. Field of the Invention

The present invention relates to a process for preparing or modifying a hydrogel (a gel containing water) by freezing and then thawing an aqueous solution of a polyvinyl alcohol, and more particularly to a process for improving mechanical strengths of a hydrogel made of a frozen polyvinyl alcohol gel.

2. Prior Art

The process for the preparation of a hydrogel comprising the step of freezing an aqueous solution of polyvinyl alcohol optionally added with an alcohol followed by thawing has been well-known in the art, for example, by Japanese Patent Publication No. 12854/1972 and U.S. Pat. No. 3,875,302 (1975). However, the gel prepared by this known process is too soft and weak and is continuously swollen for a long time to become far softer when it is dipped in water. Particularly, a gel prepared from a polyvinyl alcohol having a relatively low degree of hydrolysis or low polymerization degree or prepared from a starting aqueous solution which is low in concentration of polyvinyl alcohol, becomes so softer as to collapse to lose its integrity within a short period of time when it is dipped in water. The known gel, i.e. the hydrogel prepared through the step of freezing and subsequent thawing, has disadvantages that it is too soft and adhesive and tends to become softer by swelling, as described above, and these disadvantages are the common problems of the gels prepared from commercially available polyvinyl alcohols irrespective of the degree of hydrolysis, polymerization degree and concentration thereof. Because of these disadvantages, the prior art hydrogels of polyvinyl alcohol can be used only for limited applications, such as artificial bait, in which the softness and swelling tendency in water do not raise serious problems.

An antecedent proposal for improving mechanical strengths of a hydrogel of polyvinyl alcohol has been made by one of the inventors of this invention and is disclosed in copending U.S. application Ser. No. 400,821, filed on July 22, 1982, now abandoned. The proposal resides in the provision of a process for the preparation of a gel for use as a cooling medium, comprising the steps of casting an aqueous solution containing a polyvinyl alcohol having a degree of hydrolysis of not less than 95 mol% and a viscosity average polymerization degree of not less than 1500 into a mold having desired shape and dimensions, cooling the cast aqueous solution to a temperature of not higher than $-6°$ C., and then dehydrating in vacuum until the percentage dehydration rate reaches not less than 5 wt%. The process of this prior-made proposal indispensably involves the step of dehydrating in vacuum, and thus there are some disadvantages that dehydration of the hydrogel is not thoroughgoing enough due to small exposed surface area when it is desired to form a mass or article of special shape. For instance, when it is desired to mold an elongated pipe from the hydrogel of polyvinyl alcohol according to the known process including the step of dehydration in vacuum, an aqueous solution of a polyvinyl alcohol is cast in a mold of concentric double pipe and subjected to dehydration in vacuum after being cooled. However, since the exposed surface areas of the mass to be dehydrated are only the small end edges of the cylindrical mass, effect of vacuum dehydration is not exerted deeply enough into the internal portions of the mass, leading to unsatisfactory strength of the product hydrogel.

Hydrogels are, in general, expected as extremely favourable materials for medical uses, since they cause little damage on living tissues and are high in permeability to various substances and improved in anti-thrombotic property with the increase in water content. However, serious problems of inferior mechanical strengths of the product hydrogel in water and of less hardness of the product hydrogel hinder comprehensive uses thereof for medical materials.

OBJECTS AND SUMMARY OF THE INVENTION

A primary object of this invention is to provide a process by which a hydrogel of polyvinyl alcohol having improved mechanical strengths may be prepared without the need of dehydration in vacuum.

Additional object of this invention is to provide a process by which the frozen product hydrogel of polyvinyl alcohol is prevented from becoming too soft and also diminished in swelling rate.

Another object of this invention is to provide a process by which a frozen hydrogel of polyvinyl alcohol having improved mechanical strengths and having a utility for use as a medical material which is harmless to living bodies, may be prepared without the need of chemical treatment or irradiation of radioactive rays.

A further object of this invention is to provide a process by which a frozen hydrogel of polyvinyl alcohol having improved mechanical strengths and high water content may be prepared.

Accordingly, the present invention resides in an improvement in the process for preparing a hydrogel wherein an aqueous solution of polyvinyl alcohol is frozen followed by thawing, the improvement comprising a freezing step of freezing an aqueous solution containing 6 wt% or more of a polyvinyl alcohol having a degree of hydrolysis of not less than 95 mol% and an average polymerization degree of not less than 700 at a temperature of not higher than $-3°$ C. to obtain a frozen mass, a thawing step of thawing said frozen mass at a temperature of not higher than 55° C., and at least one additional cyclic processing step including said freezing and thawing steps. The mechanical strengths of the product hydrogel is increased by the process of the invention.

DESCRIPTION OF THE INVENTION

The above and other objects of this invention will become apparent from the following detailed description of the invention.

The polyvinyl alcohol used in the present invention should have a degree of hydrolysis of not less than 95 mol%, preferably not less than 98 mol%. The object of this invention cannot be attained by the use of a polyvinyl alcohol having a degree of hydrolysis of less than 95 mol%, for example 80 to 88 mol% particularly 85 mol%, the hydrogel prepared therefrom being a soft and fragile gel.

The polymerization degree of the polyvinyl alcohol used in the invention should be not less than 700. If the polymerization degree of the used polyvinyl alcohol is, for example less than 500, particularly less than 300, only formed is a viscous solution or a soft and fragile gel. In the present invention, a polyvinyl alcohol having a polymerization degree of, for example about 800 to 3,300 may be used, and a commercially available polyvinyl alcohol of high polymerization degree grade having a polymerization degree of 1,000 to 2,600 may be used without any pre-treatment.

In the process of the present invention, an aqueous solution containing 6 wt% or more of a polyvinyl alcohol should be prepared. The concentration of polyvinyl alcohol in the solution may preferably range within 6 to 25 wt%. The concentration of polyvinyl alcohol may be increased up to about 90 wt% or more. However, at such high concentration, some difficulties arise in handling the solution, such as excessively high viscosity of the aqueous solution at ambient temperature, for example beyond 10,000 cP., adverse increase in viscosity during storage time or occasional gelation. Although the effect of the invention may be demonstrated even when the concentration of polyvinyl alcohol is decreased less than 6 wt%, the produced gel is too soft for the aimed applications.

According to the present invention, the thus prepared aqueous solution of polyvinyl alcohol is then cast or poured into a vessel or mold having desired shape and dimensions followed by molding by freezing. Examples of the cooling medium used in this freezing step include cryogens, such as sodium chloride-ice (23:77) for cooling to $-21°$ C., calcium chloride-ice (30:70) for cooling to $-55°$ C. or combination of dry ice-methyl alcohol for cooling to $-72°$ C. and the use of liquefied nitrogen ($-196°$ C.). The mass contained in the mold should be cooled to a temperature of not higher than $-3°$ C.. The mechanical strengths of the gel become inferior if the mass contained in the mold is not cooled to a temperature low enough as defined in the appended claims. Although the content in the mold may be cooled to $-269°$ C. by the use of liquefied helium, the quality of the produced gel is not improved further, with increase in production cost. Accordingly, in practical operation, it is recommendable to use a Freon freezer to cool the mass to a temperature of, for example from $-10°$ C. to $-80°$ C.

The cooling rate at the freezing step of the process of the invention may be either of the slow cooling at a rate of 0.1° C./min. to 7° C./min., or the cooling at a rate of 7° C./min. to 50° C./min. A preferred cooling rate ranges between 1° C./min. and 40° C./min.

In the process of the invention, an aqueous solution of polyvinyl alcohol may be solidified by freezing in a mold having a desired shape to form a molded mass. After confirming that the aqueous solution of polyvinyl alcohol contained in the vessel or mold has been frozen, the frozen mass is allowed to stand at a temperature of not higher than 55° C. to be thawed. The rate of thawing may be either of the slow thawing at a rate of from 1° C./min. to 3° C./min., or the rate of from 3° C./min. to 50° C./min. Preferably, thawing is effected at a temperature raising rate of from 5° C./min. to 40° C./min. The process of the invention is characterized by subjecting the once thawed mass to a further operation cycle including similar freezing and thawing steps thereby to prevent the product hydrogel from becoming too soft by the repeated freezing and thawing operations. The effect of suppression of softening or the hardening effect by these sequential operation cycles is neither recognized nor made use of by any person until we have found and utilized the phenomenon.

According to the present invention, the product hydrogel becomes less soft as the cycle number of repeated freezing and thawing is increased, and the freezing and thawing may be set to not less than 2 times depending on the desired strength of the gel. That is, after the initial freezing and thawing steps are effected, at least one additional cyclic processing step including the freezing and thawing steps is effected. Particularly significant effects obtainable by the repeated freezing and thawing, according to the invention, are exhibited by the second to tenth repeating cycles, generally the third to sixth repeating cycles, i.e. 1 to 9 additional cyclic processing steps, generally 2 to 5 additional cyclic processing steps. With this view in mind and in consideration of cost required for the repeating cyclic operations, the mass contained in the mold may be subjected to repeated freezing and thawing cycles as many times as set by a person having ordinary skill in the art. This unique effect obtained by the repeated freezing and thawing treatments depends on the specific kind of the used polyvinyl alcohol. For example, the most effective improvement is observed by the fourth, third and second cycle, respectively, for a polyvinyl alcohol having an average polymerization degree of 1,100 to 2,000, 2,200 to 2,600 and 3,300, whereby a hydrogel containing water in increased content and not suffering from swelling in water is prepared.

According to the process of the invention, a gel containing water may be formed by the solidification of the aqueous solution of polyvinyl alcohol in its entirety. In spite of the fact that the hydrogel prepared by the invention contains a large quantity of water, the hydrogel is tough and resilient so that it restores the molded shape and dimensions to retain its integrity left unchanged by the removal or release of applied force even after it is temporarily deformed, for example, by grasping it by hand. Further, when an adult put his foot or feet on a gel of plate shape prepared in accordance with the process of the invention and containing 88 wt% of water, the gel plate is temporarily deformed by the applied weight but is immediately restored to its initial thickness and shape not to leave any deformation.

In the art of high polymer membranes for medical uses and development of permeable membranes having selectivity, it has been recognized that the provision of an increased water content material is an incompatible theme with the provision of a material having excellent mechanical strengths. However, the hydrogel prepared in accordance with the present invention has an increased water content and excellent mechanical strengths as described above, and is thus patentably differentiated from the prior art membrane prepared by air-drying an aqueous solution of polyvinyl alcohol and from the conventional water-soluble gel obtained by simply storing an aqueous solution of polyvinyl alcohol at 0° C. to 30° C. and from the known frozen gel prepared by a simple freezing process.

The hydrogel according to the invention releases little water even when a pressure is applied thereon. For instance, when a compressive stress of 4 kg/cm$^2$ is applied on a hydrogel prepared by the process of the invention and containing 90 wt% of water, only 1 to 2 wt% of the contained water is oozed therefrom. As should be apparent from the fact that the hydrogel prepared by the invention firmly holds a large quantity of water therein, the apparent specific gravity thereof is substantially same as that of water so that it slowly sinks under water.

The hydrogel prepared by the invention is not adhesive. About 10 grams for each of the hydrogels prepared by the invention was molded in the form of a plate (8 mm×8 mm×2 mm), a cylinder (having an inner diameter of 3 mm, an outer diameter of 6 mm and a length of 6 mm) and a sphere (having a diameter of 4 mm), and immersed in 50 ml of water for 40 days under agitation to reveal that no mutual adhesion or deformation of the individual masses is observed. After dipping in tap water for one year, no appreciable change in resiliency and strength was observed. This is in keen contrast to the case of KONNYAKU (devil's-tongue) which collapses seriously when it is dipped in tap water only for several days. The hydrogel prepared by the invention also exhibits the feature or properties which are in keen contrast to those of the gel prepared by simply cooling or freezing an aqueous solution of polyvinyl alcohol, the latter being highly adhesive and frequently forming a fluidized viscous liquid similar to jelly, custard pudding or agar at best to be poor in water-proof property and to have a tendency of being dispersed or dissolved in water.

In the present invention, a polyvinyl alcohol is used singly as the material for forming a gel or the gelation component. However, an inorganic and/or organic substances which do not hinder gelation of the polyvinyl alcohol may be present. The quantity of such a coexistent substance may be, for example, less than one half of the quantity of polyvinyl alcohol.

Examples of coexistent inorganic or organic substance which does not hinder gelation of the polyvinyl alcohol include activated charcoal, zeolite, heparin (in the form of sodium or calcium salt) which may be described in detail hereinafter, alcohols such as ethylene glycol, propylene glycol, methyl alcohol or glycerin, enzymes, micro-organisms and saccharose. Further examples of coexistent additives include polysaccharides and proteins such as agar, agarose, albumin, alginic acid and derivatives thereof, curdlan, carrageenan, casein, sodium cellulose glycolate, furcellaran, gelatine, methyl cellulose, pectin, starch, tamarind gum, tragacanth gum, xanthane gum and guar gum. The product hydrogel may be improved in ridigity by the addition of ethylene glycol, propylene glycol, glycerin, methyl alcohol, saccharose, glucose, agar, casein, agarose, alginic acid, carrageenan, sodium cellulose glycolate, gelatin, methyl cellulose, pectin, tragacanth gum xanthane gum or guar gum. The addition of activated char, zeolite, heparin, ethylene glycol, propylene glycol, glycerin, medicines, agricultural chemicals or fertilizers has a significant meaning when the product hydrogel is applied for use as an adsorption type artificial kidney, anti-thrombotic medical materials, anti-coagulative cooling medium or devices for sustained-release of chemicals, as will be described in detail hereinafter.

Since the hydrogel prepared by the invention includes a large quantity of water, it functions similarly to water or ice and may be used as a non-fluidized, rubber-like cooling medium in substitution for cold water or ice. For example, it may be molded in the form of rectangular parallelepiped to be used as an ice or water pillow, in the form of a sheet which is sewn to prepare cooling garments, or in the form of a disc or cone from which a cooling pad for applying, for example on a breast of a patient suffering mammary plegmasia to cool that portion may be sewn or otherwise prepared.

A gel including both of water and a polyhydric alcohol may be prepared by dipping and immersing the gel prepared by the invention into ethylene glycol, propylene glycol or glycerin or by adding one or more of these polyhydric alcohols to the aqueous solution of polyvinyl alcohol prior to the preparation of the gel. The thus prepared hydrogel is a gel including therein an antifreezing solution and may be used as an anti-coagulative or anti-hardening cooling medium to cool the head, forehead and face of a patient. An aqueous solution of a polyvinyl alcohol added with a polyhydric alcohol, such as propylene glycol, glycerin or sorbitol, may be processed through the process of the invention to prepare a molded product of membrane or net form which is used to cover the part affected by burnt wound.

The hydrogel prepared by the invention is superior to the conventional hydrogel for medical uses, i.e. the hydrogel of poly(2-hydroxyethyl) methacrylate which contains, in general, 38 to 40 wt% of water (see S. D. Bruck, Biomed. Mater. Res., 7, 387 (1973)), in that the water content of the former may be increased appreciably and the mechanical strengths of the former is improved over those of the latter.

Sodium heparin or calcium heparin which is well-known as an anti-thrombotic agent (namely an agent for preventing blood coagulation) may be included in the hydrogel prepared by the invention. Heparin is slowly released out of the hydrogel, and by the use of a gel including heparin in an amount of 4,800 unit (30 mg)/g-gel, abrupt formation of thrombus at the interface of the hydrogel of the invention contacting with blood can be prevented over a period of four weeks since the included heparin is continuously released from the hydrogel.

It should be appreciated that the hydrogel prepared by the process of the invention and including heparin therein has a remarkable advantage when used as a material for medical treatment because of its capacity of releasing heparin slowly and continuously for a long time, in view of the fact that heparin included in the known gel of polyvinyl alcohol cross-linked by an aldehyde is released generally within about 5 to 8 days entirely (in this connection, reference should be made to K. W. Merrill et al., J. Appl. Physiol., 29, 723 (1970) and N. A. Peppas et al., J. Biomed. Mater. Res., 4, 423 (1977)). The hydrogel prepared by the invention may be easily molded to have a desired shape, for example, in the form of a pipe having a diameter of from 3 to 6 mm to be used as an artificial blood vessel. The existing artificial blood vessel made of a polyester or Teflon (Trade Name) is adversely affected by serious thrombus formation, and thus hardly used as a substituent for a fine artery having a diameter of less than 5 mm or a substituent for a vein through which blood flows at a low flow rate. In contrast thereto, it has been confirmed by an experiment using dogs as the test animals that thrombus is not formed at least for one month when the gel with or without the included heparin prepared by the process of the invention is used to substitute for the artery having a diameter of 4 mm and that living tissues have adhered firmly in the vicinity of the gel of the invention to reveal that the gel prepared by the invention is compatible with the living tissues.

Other than heparin referred to above, the hydrogel prepared by the invention may include and release slowly over a long period a variety of medicines, such as pilocarpine, progesterone or carcinostatic substances, for example, 5-fluorouracil, agricultural chemicals, such as pyrethrin, sex hormones or 2,2-dichlorovinyldimethyl phosphate, and fertilizers, such as tetramethylenepentaurea, isobutylidenediurea, oxamide or 2-oxy-4-methyl-6-ureidohexahydropyrimidine.

Activated char may be included in the hydrogel prepared by the invention. It has been proposed to use a hydrogel made of gelatine or poly(2-hydroxyethyl methacrylate) and coated with activated char as an adsorption-type artificial kidney in place of dialysis usng Cuprophan. The hydrogel prepared by the invention may be, of course, coated with activated char and has mechanical strengths including abrasion-proof property superior to those of gelatine and poly(2-hydroxyethyl methacrylate) so that it provides more advantageous material for such purpose in prevention of leakage of activated char.

It has been conventionally tried to prepare a gel including therein an organic substance having a physiological activity, such as porphyrin, hemoglobin, chloroplast or enzymes, through a gelation process comprising the step of irradiating radioactive rays on an aqueous solution of polyvinyl alcohol or the step of using a cross-linking agent, such as glutaraldehyde, for cross-linking the polyvinyl alcohol molecules. The hydrogel prepared by the invention may, of course, include these organic substances. Since it need neither use gamma ray, any reagent or a catalyst such as an acid or alkali nor apply any thermal treatment in the gelation step of the process of the invention, the physiologically active substance is not damaged, and particularly the high order structure of proteins is retained in the initial state to be captured or included as it is.

The hydrogel membrane prepared by the process of the invention may be used as a substituent material for diaphragm, pericardium or dura mater, and also has a utility when used as a membrane for the prevention of adhesion between living tissues. It may be molded in the form of a pipe to be used for artificial organs of generally hollow tube such as an artificial esophagus, artificial trachea or artificial intestines, or may be coated on a silicone resin tube, polyester tube, tantalum gauze or stainless steel net to reduce considerably the foreign body reaction caused thereby.

An aqueous solution of a polyvinyl alcohol may be poured into a bag made of a silicone resin or a polyvinyl chloride followed by sealingly closing the bag, and then subjected to repeated freezing and thawing steps according to the present invention, whereby a gel which may be used for breast prosthesis or as a substituent for an ice pillow is formed.

Although it is not made clear why the flabbiness or feebleness of the frozen gel is diminished extremely together with loss of adhesiveness and reduction of swelling in water by subjecting the gel to repeated freezing and thawing operations two or more times, these advantageous effects were not known until we found the effects and made use thereof.

EXAMPLES OF THE INVENTION

EXAMPLE 1

141 g of a commercially available polyvinyl alcohol powder (Water Content: 8 wt%) having a degree of hydrolysis of 99.4 mol%, an average polymerization degree of 2,600 and a viscosity at 20° C. of a 4% aqueous solution of 66 cP. was dissolved in 725 g of water to prepare a 15 wt% aqueous solution of polyvinyl alcohol. 50 g of the thus prepared solution was poured into a test tube having a diameter of 24 mm, and cooled (subjected to molding by freezing) at a cooling rate of 3° C./min. to reach $-15°$ C. and maintained at that temperature for 7 hours followed by thawing at a rate of 1° C./min. to reach 25° C. and allowed to stand the mass at that temperature for 4 hours, whereby Sample 1A was prepared which was a white, opaque and soft gel (Weight: 50 g). Sample 1A was contained in a polyethylene pouch which was sealingly closed, and then the content in the pouch was again subjected to freezing and thawing operations conducted under the conditions similar to the preceding cycle, whereby sample 1B was prepared. Sample 1B was subjected to a further freezing step conducted under the conditions similar to the preceding freezing steps followed by thawing at ambient temperature, whereby Sample 1C was prepared. Sample 1C was wrapped with a filter paper (Toyo Roshi #5A, Diameter: 18.5 cm) to find that it did not adhere and stick to the surface of filter paper. 10.0 g of Sample 1C was dipped in water and the change in weight and the swelling behavior thereof with the lapse of time were observed. The results are shown in the following Table 1.

TABLE 1

| Lapse of Time (days) | 0 | 1 | 2 | 3 | 4 | 5 | 6 | 7 |
|---|---|---|---|---|---|---|---|---|
| Weight (g) | 10 | 11 | 11 | 11 | 11 | 11 | 11 | 11 |
| Swelling Rate | 1.0 | 1.1 | 1.1 | 1.1 | 1.1 | 1.1 | 1.1 | 1.1 |

The dynamic visco-elasticity of Sample 1C was determined separately. The results are shown in Table 2.

TABLE 2

| Temperature (°C.) | 15 | 25 | 35 | 45 | 55 | 75 |
|---|---|---|---|---|---|---|
| Storage Modulus E' (N/m$^2$) | $1 \times 10^5$ | $1.1 \times 10^5$ | $1.2 \times 10^5$ | $1.1 \times 10^5$ | $0.9 \times 10^5$ | $6 \times 10^3$ |

Note:
Storage Modulus was determined in accordance with the method by Katsuyoshi Nishinari et al., Nippon Shokuhin Gakkaishi, 27, (5) 227, (1980).

COMPARATIVE EXAMPLE 1

Sample 1A was prepared by repeating the procedure as set forth in Example 1, and the sample was subjected to the filter paper adhesion test as described in Example 1. The result was that the tendency of adhering onto the surface of filter paper was observed obviously. The results of the test wherein the sample was dipped in water are shown in Table 3, and the results of the determination of storage modulus are shown in Table 4.

TABLE 3

| Lapse of Time (days) | 0 | 1 | 2 | 3 | 4 | 5 | 6 | 7 |
|---|---|---|---|---|---|---|---|---|
| Weight (g) | 10 | 11 | 12 | 12 | 12 | 12 | 12 | 13 |
| Swelling Rate | 1.0 | 1.1 | 1.2 | 1.2 | 1.2 | 1.2 | 1.2 | 1.3 |

TABLE 4

| Temperature (°C.) | 15 | 25 | 35 | 45 | 55 | 65 |
|---|---|---|---|---|---|---|
| Storage Modulus E' (N/m$^2$) | $1.1 \times 10^4$ | $1.2 \times 10^4$ | $1.3 \times 10^4$ | $1.2 \times 10^4$ | $1 \times 10^4$ | $0.7 \times 10^4$ |

As will be readily seen from the Tables, Sample 1C prepared in Example 1 according to the process of the invention wherein the mass was subjected to repeated three cycle freezing and thawing steps did not adhere to filter paper, was not suffered from significant swelling even when dipped in water and had an E' value (N/m$^2$) at 15° to 55° C. of in the order of $10^5$, whereas the sample prepared by the process similar to the conventional technology (Sample 1A) adhered to filter paper, was swollen to have a volume of 1.3 times as large as the initial volume by dipping the same in water for 7 days to be softened and had a relatively low E' value of in the order of $10^4$. Also, the finger touch test conducted by pressing the product gels by finger revealed that Sample 1C was improved over Sample 1A in reduction of softness or flabbiness.

EXAMPLE 2

86 g of a commercially available polyvinyl alcohol powder (Water Content: 7 wt%) having a degree of hydrolysis of 97 mol%, an average polymerization degree of 1,700 and a viscosity at 20° C. of a 4% aqueous solution of 28 cP. was dissolved in 914 g of water to prepare an aqueous solution containing 8.0 wt% of the polyvinyl alcohol.

Generally in accordance with the procedures described in Example 1, 51 g of the thus prepared aqueous solution was cooled at a cooling rate of 5° C./min. to reach −40° C. and maintained at that temperature for 12 hours, and then thawed at a rate of 2° C./min. to reach 23° C. and allowed to stand for 2 hours to prepare Sample 2A. Similar freezing and thawing were repeated once (for Sample 2B), twice (for Sample 2C) and thrice (for Sample 2D). Sample 2D did not adhere to filter paper and gave the results as shown in Table 5 when dipped in water:

TABLE 5

| Lapse of Time (days) | 0 | 1 | 2 | 3 | 4 | 5 | 6 | 7 |
|---|---|---|---|---|---|---|---|---|
| Weight (g) | 10 | 11 | 11 | 11 | 11 | 11 | 11 | 11 |
| Swelling Rate | 1.0 | 1.1 | 1.1 | 1.1 | 1.1 | 1.1 | 1.1 | 1.1 |

Results of determination of E' fraction of storage modulus of Sample 2D are shown in Table 6.

TABLE 6

| Temperature (°C.) | 15 | 25 | 35 | 55 | 65 | 75 |
|---|---|---|---|---|---|---|
| Storage Modulus E' (N/m$^2$) | $5 \times 10^4$ | $6 \times 10^4$ | $6 \times 10^4$ | $4 \times 10^4$ | $1 \times 10^4$ | $3 \times 10^3$ |

COMPARATIVE EXAMPLE 2

Sample 2A was prepared by repeating the procedure as set forth in Example 2, and the sample was subjected to filter paper adhesion test to reveal that the sample adhered apparently to the surface of filter paper. The results of the test wherein the sample was dipped in water are shown in Table 7, and the values of E' fraction determined by the determination of storage modulus are shown in Table 8.

TABLE 7

| Lapse of Time (days) | 0 | 1 | 2 | 3 | 4 | 5 | 6 | 7 |
|---|---|---|---|---|---|---|---|---|
| Weight (g) | 10 | 12 | 13 | 14 | 14 | 15 | 15 | 15 |
| Swelling Rate | 1.0 | 1.2 | 1.3 | 1.4 | 1.4 | 1.5 | 1.5 | 1.5 |

TABLE 8

| Temperature (°C.) | 15 | 25 | 35 | 45 | 55 | 65 |
|---|---|---|---|---|---|---|
| Storage Modulus E' (N/m$^2$) | $5 \times 10^3$ | $6 \times 10^3$ | $6 \times 10^3$ | $6 \times 10^3$ | $4 \times 10^3$ | $1.1 \times 10^3$ |

As will be readily seen by comparing the results of Example 2 with those of Comparative Example 2, Sample 2D prepared by Example 2 according to the present invention by subjecting the molded mass to freezing and thawing steps repeatedly for four times did not adhere to filter paper, was not suffered from significant swelling and had an E' value (N/m$^2$) at 15° to 65° C. of in the order of $10^4$, whereas the frozen gel (Sample 2A) which was prepared by a process other than the process of the invention adhered to filter paper, was swollen to have a volume of 1.5 times as large as the initial volume by dipping the same in water for 7 days and had so low E' value (N/m$^2$) as in the order of $10^3$. Also, the finger touch test conducted by pressing the product gels by finger revealed that Sample 2D was improved over Sample 2A in reduction of softness of flabbiness.

EXAMPLE 3

Generally in accordance with the procedures as described in Example 1, 60 g of a 15 wt% aqueous solution of a polyvinyl alcohol having an average polymerization degree of 2,400 and a degree of hydrolysis of 99.6 mol% was cooled at a cooling rate of 2° C./min. to reach −5° C. and maintained at that temperature for 24 hours followed by thawing at a rate of 0.3° C./min. to reach 22° C. and allowed to stand for 2 hours to prepare Sample 3A. Sample 3A was subjected to similar freezing and thawing steps to prepare Sample 3B which was again subjected to next cycle freezing and thawing steps to prepare Sample 3C. Sample 3C did not adhere to filter paper and gave the results shown in Table 9 when dipped in water and the results of determination of E' fraction of storage modulus as shown in Table 10.

TABLE 9

| Lapse of Time (days) | 0 | 1 | 2 | 3 | 4 | 5 | 6 | 7 |
|---|---|---|---|---|---|---|---|---|
| Weight (g) | 20 | 21 | 21 | 21 | 21 | 21 | 21 | 21 |
| Swelling | 1.0 | 1.1 | 1.1 | 1.1 | 1.1 | 1.1 | 1.1 | 1.1 |

TABLE 9-continued

| | |
|---|---|
| Rate | |

TABLE 10

| Temperature (°C.) | 15 | 25 | 35 | 45 | 55 | 65 |
|---|---|---|---|---|---|---|
| Storage Modulus E' (N/m$^2$) | $0.8 \times 10^5$ | $1 \times 10^5$ | $1.1 \times 10^5$ | $1 \times 10^5$ | $0.7 \times 10^5$ | $0.5 \times 10^5$ |

COMPARATIVE EXAMPLE 3

Sample 3A was prepared by repeating the procedures as described in Example 3, and the sample was subjected to filter paper adhesion test to reveal that the sample adhered to the surface of filter paper obviously. The results of the test wherein the sample was dipped in water are shown in Table 11, and the values of E' fraction determined by the determination of storage modulus are shown in Table 12.

TABLE 11

| Lapse of Time (days) | 0 | 1 | 2 | 3 | 4 | 5 | 6 | 7 |
|---|---|---|---|---|---|---|---|---|
| Weight (g) | 20 | 25 | 27 | 28 | 29 | 30 | 30 | 30.5 |
| Swelling Rate | 1.0 | 1.3 | 1.3 | 1.4 | 1.5 | 1.5 | 1.5 | 1.5 |

TABLE 12

| Temperature (°C.) | 15 | 25 | 35 | 45 | 55 | 65 |
|---|---|---|---|---|---|---|
| Storage Modulus E' (N/m$^2$) | $0.8 \times 10^4$ | $1 \times 10^4$ | $1.1 \times 10^4$ | $1.1 \times 10^4$ | $0.8 \times 10^4$ | $0.6 \times 10^4$ |

As will be readily seen by comparing the results of Example 3 with those of Comparative Example 3, Sample 3C prepared by Example 3 according to the present invention by subjecting the molded mass to freezing and thawing steps repeatedly for three times did not adhere to filter paper, was not suffered from significant swelling and had an E' value (N/m$^2$) at 15 to 65° C. of in the order of $10^5$, whereas the frozen gel (Sample 3A) which was prepared by a process other than the process of the invention adhered to filter paper, was swollen to have a volume of 1.5 times as large as the initial volume by dipping the same in water for four days and had so low E' value (N/m$^2$) as in the order of $10^4$. The finger touch test conducted by pressing the product gels by finger revealed that Sample 3C was appreciably improved over Sample 3A in reduction of softness or flabbiness.

COMPARATIVE EXAMPLE 4

40 g of a 15 wt% aqueous solution of a polyvinyl alcohol having an average polymerization degree of 1,100 and a degree of hydrolysis of 99.5 mol% was poured into a test tube having a diameter of 24 mm, and then cooled to −30° C. for 24 hours to obtain a frozen mass which was allowed to stand at ambient temperature for 3 hours to be thawed to prepare Sample 4A. This sample 4A was dipped in 200 ml of water which was maintained at ambient temperature to obtain the results shown in Table 13. As will be apparent from the results, the gel which was soft at the initial stage became softer by dipping in water for one week and the gel was swollen severly.

TABLE 13

| Lapse of Time (days) | 0 | 1 | 2 | 3 | 4 | 5 | 6 | 7 |
|---|---|---|---|---|---|---|---|---|
| Weight (g) | 40 | 46 | 52 | 57 | 62 | 66 | 70 | 73 |
| Swelling Rate | 1.0 | 1.2 | 1.3 | 1.4 | 1.6 | 1.7 | 1.8 | 1.8 |

EXAMPLE 4

40 g of the aqueous solution of polyvinyl alcohol prepared and used in Comparative Example 4 was subjected to steam sterilization at 120° C. for 30 minutes, and then poured into a pre-sterilized test tube having a diameter of 24 mm. The test tube was put into a polyethylene pouch sterilized by ethylene oxide gas and the pouch was then closed sealingly. The sealed pouch and the content therein was cooled at a cooling rate of 20° C./min. to reach −30° C. and maintained for 24 hours and then thawed at a rate of 10° C./min. to reach 20° C. and allowed to stand at that temperature for 3 hours. The foregoing cycle including the freezing and thawing steps was repeated for additional three times to prepare a gel (Sample 4D) according to the invention. A portion (25 g) of the thus prepared sample was dipped in water to obtain the results shown in Table 14. The sample was also subjected to finger touch test, similarly to the preceding Examples, to find that the sample was improved in reduction of softness or flabbiness over the Sample 4A.

TABLE 14

| Lapse of Time (days) | 0 | 1 | 2 | 3 | 4 | 5 | 6 | 7 |
|---|---|---|---|---|---|---|---|---|
| Weight (g) | 25 | 26 | 27 | 27 | 27 | 27 | 27 | 27 |
| Swelling Rate | 1.0 | 1.0 | 1.1 | 1.1 | 1.1 | 1.1 | 1.1 | 1.1 |

A fragment having a diameter of 21 mm and a thickness of 5 mm was cut from the Sample 4D in a germ-free chamber, and dipped in Hibitane solution for one night followed by rinsing with a sterilized physiological saline solution to prepare a test speciment to be embedded into a living body.

The furs at the back of a rabbit (Weight: 2.5 kg) were shaven off, and a 0.5% chlorohexidine (bis-(p-chlorophenyldiguanido)-hexane) solution in ethyl alcohol was coated on the exposed skin which was then sterilized using a 70% ethyl alcohol solution. The thus sterilized skin was incised by about 1.5 cm, and the aforementioned test specimen was buried under the incised skin which was then sewn to be closed. During this operation, attention was paid so that the incised line along the skin was not overlapped with the buried test specimen. In view of the observation after 24 hours, rubefaction and slight tumefaction or oncoides were found and the buried test specimen was movable within the peeled area beneath the skin by touching the specimen through the surface of the skin. Rubefaction and tumefaction disappeared after the lapse of 4 days, and the stitches were extracted after the lapse of 6 days. The test specimen had been fixed and could not be moved by touching from the outside after the lapse of 9 days. Continuing the observation for additional one week, no change was found at the portion buried with the test specimen and no general disorder was observed. The test specimen was took out together with skin tissues after the lapse of additional 15 days and observed. The results of observation were that the test specimen had been enclosed by connective tissues, that no mutual adhesion was observed between the test specimen and the connective tissues, and that the test specimen was closely fitted by the connective tissues. These connective tissues were treated by a 10% formalin for fixation wrapped in paraffin, and subjected to the hematoxylin and eosin stain test and the van Gieson stain test. It was observed that cellular infiltration was extremely slight and inflammation reactions were negligible although a small numbers of pseudo-acidocytes and round cells were found.

On the other hand, strong foreign body reaction was observed in the vicinities of the catgut used as the sewing stitches even after the stitches had been extracted. For the comparison purpose, a 20 mm×13 mm×5 mm piece of natural sponge was buried under the skin of a rabbit at the back thereof. It took 14 days for disappearance of rubefaction and tumefaction, and in view of the results of observation on the taken-out specimen after the lapse of 2 weeks, the dimensions of the sponge were decreased by about 10%, serious cellular infiltration and a number of foreign body giant cells were found in the vicinity of the buried sponge, and the portion buried with the sponge was affected by purulent sore. A similar comparison experiment was conducted using a test specimen made of a methyl methacrylate resin, the results being that it took one week for disappearance of rubefaction and tumefaction and serious cellular infiltration by the pseudo-acidocytes was observed. It should be appreciated from the results referred to hereinabove that the hydrogel prepared by the process of the invention is remarkably improved in compatibility to living tissues without attendant adhesion.

COMPARATIVE EXAMPLE 5

30 g of a 10% aqueous solution of a polyvinyl alcohol having an average polymerization degree of 3,300, a degree of hydrolysis of 99.7 mol% and a viscosity at 20° C. of a 4% aqueous solution of 125 cP. was poured into a test tube having a diameter of 24 mm, and cooled to −20° C. for 12 hours and allowed to stand at ambient temperature for 3 hours to prepare Sample 5A. Sample 5A was dipped in 200 ml of water at ambient temperature to obtain the results shown in Table 15 which showed the tendency of swelling of the sample.

TABLE 15

| Lapse of Time (days) | 0 | 1 | 2 | 3 | 4 |
|---|---|---|---|---|---|
| Weight (g) | 30 | 33 | 34 | 34 | 35 |
| Swelling Rate | 1.0 | 1.1 | 1.1 | 1.1 | 1.2 |

EXAMPLE 5

30 g of the aqueous solution of polyvinyl alcohol as used in Comparative Example 5 was subjected to repeated freezing and thawing steps for two cycles, similarly to Example 4, to obtain Sample 5B of the hydrogel prepared by the present invention. A portion of the sample (29 g) was dipped in water to obtain the results shown in Table 16 and to confirm that it had no tendency of swelling, and was subjected to the finger touch test to reveal that the softness or flabbiness thereof was diminished.

TABLE 16

| Lapse of Time (days) | 0 | 1 | 2 | 3 | 4 | 5 | 6 | 7 |
|---|---|---|---|---|---|---|---|---|
| Weight (g) | 29 | 30 | 30 | 30 | 30 | 30 | 30 | 30 |
| Swelling Rate | 1.0 | 1.0 | 1.0 | 1.0 | 1.0 | 1.0 | 1.0 | 1.0 |

A fragment having a diameter of 21 mm and a thickness of 4 mm was cut from Sample 5B in a germ-free chamber, and dipped in Hibitane solution followed by rinsing with a sterilized physiological saline solution to prepare a test specimen to be buried into a living body.

A rabbit (Weight: 2.5 kg) was subjected to an operation of longitudinal incision by 3 cm of the interior skin of medial knee joint and of longitudinal incision of the skin interior of medial musclus quadriceps fermoris followed by dislocation of patella and bending the knee joint, and the adipose tissue of the anterior surface was cut off by abscission and the crossed ligamentum was cut by ablatio. Thereafter, the joint capsules other than the posterior joint capsule and the meniscus were cut off by abscission. Then, the femur arthrodial cartilage was removed and the test specimen prepared as described hereinbefore was inserted and fixed on the femur articular surface in place of said femur arthrodial cartilage. The leg portion from the upper portion of thigh to the foot was tied by plaster bandage while the knee joint was flexed at an angle of 150 degrees, and the bandage was removed after the lapse of 3 weeks from the operation. At that point of time, tumefaction to slight extent was observed but no rubefaction or local pyrexia was observed. Favorable primary coaptation was observed with no significant secreting fluid, and the knee joint was held at an angle of about 120 degrees to show protected limping gait. The knee joint could be moved in the range of from 150 degrees to 90 degrees. A specimen of the tissue was taken and subjected serially to fixation by formalin, wrapping with paraffin, dyeing by hematoxyline and eosin stain, and dyeing by Mallory azan staining. The thus treated specimen was observed through a microscope to find that the articular surface of femur was covered by the tela conjunctive, and that no ossein hyperplasia and no inflammation of medullary space due to the action of inserted specimen was observed.

Separately, a similar comparison experiment was conducted using a fragment made of a methylmethacrylate resin having a thickness of 1.5 mm. In view of the observation after the lapse of 3 weeks, tumefaction and local pyrexia were observed at the joint part, and pulsating motion or palpation was observed at the portion above the patella by examination by touch. Although the knee joint could be moved within a narrow angular range when it was moved passively after the plaster bandage was removed, positive joint motion was so little as negligible. Inflammatory cellular infiltration and fibrous cicatrization were found at articular surface of femur. It should be appreciated from the observations set forth above that the hydrogel prepared by the invention is improved in compatibility with living body.

EXAMPLE 6

A 15 wt% aqueous solution of polyvinyl alcohol was prepared by dissolving 140 g of a polyvinyl alcohol powder (Water Content: 7 wt%) having an average polymerization degree of 2,500, a degree of hydrolysis of 99.7 mol% and a viscosity at 20° C. of a 4% aqueous solution of 67 cP. in 725 g of water. The thus prepared aqueous solution was poured into a mold for molding a pipe, and cooled at a cooling rate of 5° C./min. to −25° C. and allowed to stand at that temperature for 12 hours. Then, the frozen mass was heated at a temperature raising rate of 3° C./min. to 25° C. and then allowed to stand at that temperature for 3 hours to be thawed, whereby Sample 6A was prepared. A white, opaque and soft pipe was formed by the foregoing operations, the pipe having an inner diameter of 12 mm, an outer diameter of 15 mm and a length of 6 cm, but the pipe had so low dynamic modulus E' of $0.2 \times 10^5$ N/m$^2$ (at 25° C.). The soft pipe was subjected to repeated operation cycles each including similar freezing and thawing steps to obtain Samples 6B, 6C, 6D, 6F, 6G and 6H. The dynamic modulus E' of each of the Samples was determined to obtain the results shown in Table 17.

TABLE 17

| Sample No. | 6A | 6B | 6C | 6D | 6E | 6F | 6G | 6H |
|---|---|---|---|---|---|---|---|---|
| E' ($\times 10^5$ N/m$^2$) | 0.2 | 0.4 | 0.8 | 1.2 | 1.7 | 1.9 | 2.0 | 2.5 |

It should be readily understood from the Table 17 set forth just above, that the dynamic modulus may be increased to 12.5 times as high as the initial value by the repeated freezing and thawing operations and a pipe excellent in integrity or shape-retention property may be obtained by the process of the invention. The pipe was dipped in Hibitane solution for one night followed by rinsing with a sterilized physiological saline solution, and then used as an artificial trachea.

A mongrel dog (Weight: 9 kg) was anesthetized by an anesthesia under the closed circulation, and its cervical trachea was exposed. After passing a silicone resin string through the outer periphery at the front side of the peripheral trachea at the position one ring below the line sought to be cut, the peripheral trachea was cut. Thereafter, the aforementioned pipe (Sample 6H) was inserted into the peripheral trachea through the cut opening and fixedly tied by said silicone resin string. A tube for delivering anesthesia gas was rapidly inserted into the lumen of said pipe to maintain the dog in the anesthetized condition. Then, the central trachea was cut through a similar procedure and the said anesthesia gas delivery tube was removed. Thereafter, the said pipe was fitted into the central trachea which was then tightly fixed by tying. The strings used for fixation of the pipe to the peripheral trachea and central trachea was bound together. An antibiotic medicine was spread over the operated area followed by sewing the incised wound, and an antibiotic medicine was dosed by intramuscular injection for two weeks.

In view of the bronchography taken after 2 months from the operation, no syrin was observed. According to the examination through a bronchoscopy, no ulcer, tumor or contraction was observed with the tracheal muscosa in the vicinities of the joined portions having normal color. No other abnormality was found. During the course of the examination conducted by the use of the bronchoscopy, a water droplet and cotten bead were inserted in the neighbourhood of the bifurcation of the trachea to confirm that the operated dog had an ability of expectration.

COMPARATIVE EXAMPLE 6

The initial procedure as described in Example 6 was repeated to prepare Sample 6A which was utilized directly, without subjecting to repeated cyclic freezing and thawing steps, as an artificial trachea through the sterilization treatment. The thus prepared pipe was implanted into the cervical trachea of a dog in the manner similar to that described in Example 6. However, the pipe was too soft to make it extremely difficult to join the same to the cervical trachea. Although the pipe was joined to the trachea while overcoming the difficulty, the operated dog was dead after 30 hours from the time of operation. In view of the examination by autopsy, it was diagnosed that the pipe had been contracted due to its inherent softness.

Although the present invention has been described with reference to some examples, it should be understood that various modifications and variations can be easily made by those skilled in the art without departing from the spirit of the invention. Accordingly, the foregoing disclosure should be interpreted as illustrative only and not to be interpreted in a limiting sense. The present invention is limited only by the scope of the following claims.

What is claimed is:

1. A process for preparing an artificial biological membrane suitable for surgical use comprising polyvinyl alcohol selected from the group consisting of diaphragm, pericardium, dura mater and membrane for the prevention of adhesion between living tissues, which process comprises a freezing step of freezing an aqueous solution containing 6 wt% or more of a polyvinyl alcohol having a degree of hydrolysis of not less than 95 mol% and an average polymerization degree of not less than 700 at a temperature of not higher than −3° C. to obtain a frozen mass, a thawing step of thawing said frozen mass at a temperature of not higher than 55° C., and at least one additional cyclic processing step including said freezing and thawing steps, said aqueous solution of said polyvinyl alcohol containing at least one of an inorganic substance and an organic substance which does not hinder gelation of said polyvinyl alcohol.

2. A process for preparing an artificial biological membrane suitable for surgical use comprising polyvinyl alcohol selected from the group consisting of diaphragm, pericardium, dura mater and membrane for the prevention of adhesion between living tissues, which process comprises a freezing step of freezing an aqueous solution containing 6 wt% or more of a polyvinyl alcohol having a degree of hydrolysis of not less than 95 mol% and an average polymerization degree of not less than 700 at a temperature of not higher than −3° C. to obtain a frozen mass, a thawing step of thawing said frozen mass at a temperature of not higher than 55° C., and at least one additional cyclic processing step including said freezing and thawing steps, said aqueous solution of said polyvinyl alcohol containing one or more selected from the group consisting of activated charcoal, zeolite, heparin, alcohols, enzymes, microorganisms, saccharose, polysaccharides, proteins, medicines and mixtures thereof.

3. The process according to claim 2, wherein said aqueous solution of said polyvinyl alcohol contains heparin.

4. A process for preparing an artificial biological membrane suitable for surgical use comprising polyvinyl alcohol selected from the group consisting of diaphragm, pericardium, dura mater and membrane for the prevention of adhesion between living tissues, which process comprises a freezing step of freezing an aqueous solution containing 6 wt% or more of a polyvinyl alcohol having a degree of hydrolysis of not less than 95 mol% and an average polymerization degree of not less than 700 at a temperature of not higher than −3° C. to obtain a frozen mass, a thawing step of thawing said frozen mass at a temperature of not higher than 55° C., and at least one additional cyclic processing step including said freezing and thawing steps, said aqueous solution of said polyvinyl alcohol containing a medicine selected from the group consisting of pilocarpine, progesterone and carcinostatic substances.

5. A process for preparing an artificial biological membrane suitable for surgical use comprising polyvinyl alcohol selected from the group consisting of diaphragm, pericardium, dura mater and membrane for the prevention of adhesion between living tissues, which process comprises a freezing step of freezing an aqueous solution containing 6 wt% or more of a polyvinyl alcohol having a degree of hydrolysis of not less than 95 mol% and an average polymerization degree of not less than 700 at a temperature of not higher than −3° C. to obtain a frozen mass, a thawing step of thawing said frozen mass at a temperature of not higher than 55° C., and at least one additional cyclic processing step including said freezing and thawing steps, said aqueous solution of said polyvinyl alcohol containing an organic substance having physiological activity selected from the group consisting of porphyrin, hemoglobin, chloroplast and enzymes.

* * * * *